United States Patent [19]

Bru-Magniez et al.

[11] Patent Number: 4,886,805
[45] Date of Patent: Dec. 12, 1989

[54] NOVEL AMINOALKYLTHIO DERIVATIVES OF TRIAZOLOPYRIDINE OR TRIAZOLOQUINOLINE, THE PROCESSES FOR THEIR PREPARATION, AND DRUGS, USEFUL ESPECIALLY AS ANALGESICS, IN WHICH THEY ARE PRESENT

[75] Inventors: Nicole Bru-Magniez, Paris; Jean-Marie Teulon, La Celle Saint Cloud; Michèle Launay, Rueil-Malmaison, all of France

[73] Assignee: Centre D'Activite Et De Recherches Pharmaceutique Industrielle Biologique Medicale, Rueil-Malmaison, France

[21] Appl. No.: 72,337

[22] Filed: Jul. 10, 1987

[30] Foreign Application Priority Data

Jul. 23, 1986 [FR] France .................................. 8610709

[51] Int. Cl.$^4$ ................. A61K 31/495; A61K 31/535; A61K 31/435; A61K 31/41; A61K 31/44; A61K 31/47; C07D 403/14; C07D 401/14
[52] U.S. Cl. .................................. 514/253; 514/228.5; 514/233.2; 514/278; 514/293; 544/61; 544/125; 544/126; 544/295; 544/361; 544/362; 546/16; 546/94; 546/119
[58] Field of Search ................. 544/362, 361; 514/253

[56] References Cited

U.S. PATENT DOCUMENTS

| | | | |
|---|---|---|---|
| 4,244,953 | 1/1981 | Trust et al. ........................... | 514/303 |
| 4,340,597 | 7/1982 | Gold et al. ........................... | 514/303 |
| 4,358,453 | 11/1982 | Bristol et al. ....................... | 514/303 |
| 4,358,454 | 11/1982 | Bristol et al. ....................... | 514/303 |

FOREIGN PATENT DOCUMENTS 4039094 3/1979 Japan ................................... 514/303

OTHER PUBLICATIONS

Saito et al, Chem. Abst. 87-167944u.

Primary Examiner—Mukund J. Shah
Assistant Examiner—Cecilia Shen
Attorney, Agent, or Firm—Poms, Smith, Lande & Rose

[57] ABSTRACT

The present invention relates to novel compounds corresponding to the formula:

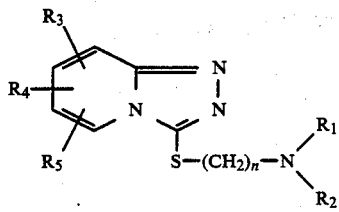

in which:

n represents an integer between 1 and 8 and optimally 2 or 3; $(CH_2)_n$—N can also form a ring or a heterocycle, for example having 5 to 7 atoms and preferably 6 atoms;

$R_1$ and $R_2$ can represent hydrogen or a lower alkyl having 1 to 5 carbon atoms or can form, together with the nitrogen, a ring such as pyrrolidine, piperidine, morpholine, thiomorpholine, phenyltetrahydropyridine, piperazine or piperazine N-substituted by an alkyl, a phenyl or a heterocycle; in the case of the phenyltetrahydropyridines and the phenylpiperazines or heteroarylpiperazines, the phenyl or the heterocycle may or may not be substituted by halogens or methoxy, thiomethyl, hydroxyl, nitro, amino, cyano, lower alkyl, trifluoromethyl or trichloromethyl groups; and $R_3$, $R_4$ and $R_5$ can represent hydrogen, a lower alkyl, a hydroxyalkyl or hydroxybenzyl group, a halogen, a trifluoromethyl, a methoxy, a thiomethyl or a nitro or two of them can form a ring, in particular a phenyl in the case of the triazoloquinolines or the triazoloisoquinolines; and the non-toxic acid addition salts.

These products are useful as drugs and possess analgesic properties, acting especially on the central nervous system as minor tranquilizers.

14 Claims, No Drawings

NOVEL AMINOALKYLTHIO DERIVATIVES OF TRIAZOLOPYRIDINE OR TRIAZOLOQUINOLINE, THE PROCESSES FOR THEIR PREPARATION, AND DRUGS, USEFUL ESPECIALLY AS ANALGESICS, IN WHICH THEY ARE PRESENT

The present invention relates to aminoalkylthio derivatives of triazolopyridine or triazoloquinoline of the formula (I). It also relates to the processes for the preparation of the said products and their applications in therapy. It further relates to the novel intermediates which enable the said products to be synthesized.

The novel compounds according to the invention are selected from the group comprising the compounds of the general formula (I):

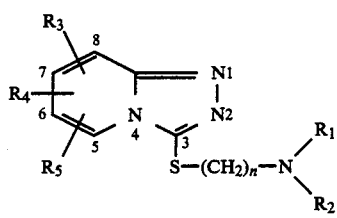

formula (I)

in which:
n represents an integer between 1 and 8 and optimally 2 or 3; $(CH_2)_n$—N can also form a ring or a heterocycle, for example having 5 to 7 atoms and preferably 6 atoms;

$R_1$ and $R_2$ can represent hydrogen or a lower alkyl having 1 to 5 carbon atoms or can form, together with the nitrogen, a ring such as pyrrolidine, piperidine, morpholine, thiomorpholine, phenyltetrahydropyridine, piperazine or piperazine N-substituted by an alkyl, a phenyl or a heterocycle; in the case of the phenyltetrahydropyridines and the phenylpiperazines or heteroarylpiperazines, the phenyl or the heterocycle may or may not be substituted by halogens or methoxy, thiomethyl, hydroxyl, nitro, amino, cyano, lower alkyl, trifluoromethyl or trichloromethyl groups; and $R_3$, $R_4$ and $R_5$ can represent hydrogen, a lower alkyl, a hydroxyalkyl or hydroxybenzyl group, a halogen, a trifluoromethyl, a methoxy, a thiomethyl or a nitro or two of them can form a ring, in particular a phenyl in the case of the triazoloquinolines or the triazoloisoquinolines; and the non-toxic acid addition salts of the compounds of the formula (I).

Some particular compounds are those in which $R_3=R_4=R_5=$hydrogen.

The preferred compounds according to the invention are those in which n=2 or 3.

Other preferred compounds are those in which $R_3=$trifluoromethyl and $R_4=R_5=$hydrogen.

Other preferred compounds are those in which $NR_1R_2$ can represent:
4-(3-trifluoromethylphenyl)piperazin-1-yl;
4-(2,4-difluorophenyl)piperazin-1-yl;
4-(3-chlorophenyl)piperazin-1-yl; or
4-(2-fluorophenyl)piperazin-1-yl.

Even greater preference is given to the compounds corresponding to the following formulae:

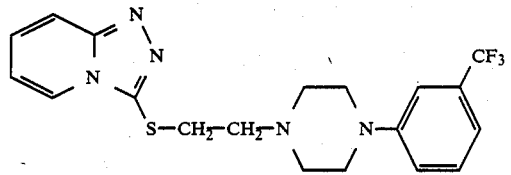

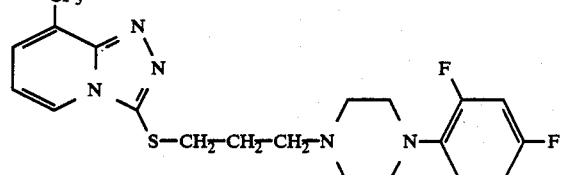

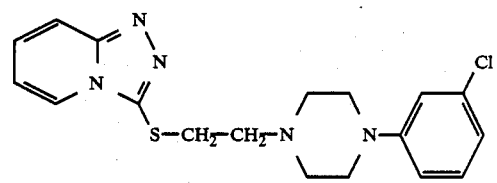

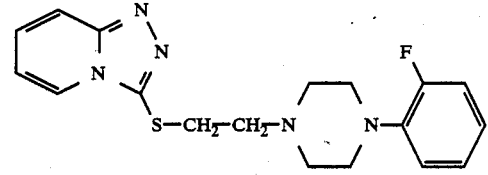

The invention also covers, as novel products, 4-(2,4-difluorophenyl)piperazine or one of its addition salts, preferably one of its non-toxic or pharmaceutically acceptable acid addition salts, this product constituting a very useful intermediate for the preparation of the products of the formula (I) above.

The present invention also covers the use of the compounds of the formula (I) above, and 4-(2,4-difluorophenyl)piperazine or one of its non-toxic acid addition salts, as drugs possessing analgesic properties and acting especially on the central nervous system as minor tranquilizers.

The compounds of the formula (I) according to the invention can be synthesized by reacting thio derivatives of the formula (II):

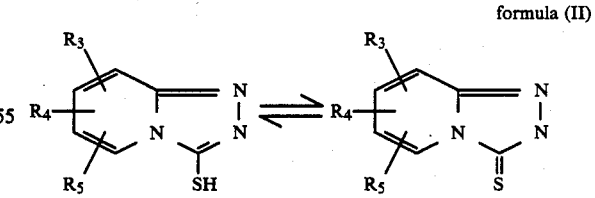

formula (II)

in which $R_3$, $R_4$ and $R_5$ are defined as above, with halogenoalkylamines tosyloxyalkylamines or mesyloxyalkylamines of the formula (III):

formula (III)

in which n, $R_1$ and $R_2$ are defined as above, X being a halogen or a good leaving group such as tosyloxy or mesyloxy.

This reaction can be carried out by metallating the thiol group with a conventional metallating agent such as sodium or lithium hydride, sodium or potassium hydroxide or sodium or potassium carbonate, or in the presence of a base such as, for example, triethylamine or pyridine, in a customary organic solvent such as benzene or toluene, an alcohol such as methanol or ethanol, dimethylformamide, N-methylpyrrolidone or dimethylacetamide, at a temperature of between 20° and 150° C.

The compounds of the formula (I) can also be prepared by reacting a compound of the formula (IV):

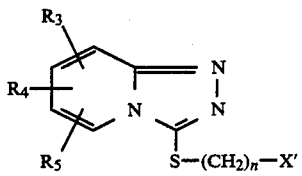

formula (IV)

in which $R_3$, $R_4$, $R_5$ and n are defined as above, X' being a halogen or a good leaving group such as tosyloxy or mesyloxy, with an amine of the formula (V):

formula (V)

in which $R_1$ and $R_2$ are defined as above, in an organic solvent such as toluene or xylene or an alcohol, in the presence of an additional molecule of amine or in the presence of triethylamine or pyridine, at between 50° and 140° C.

The compounds of the formula (IV) can be prepared by reacting dihalogenoalkanes with the compounds of the formula (II) under the same conditions as the halogenoalkylamines, or by chlorination or bromination, by conventional methods such as, for example, thionyl chloride, of the corresponding alcohols of the formula (VI):

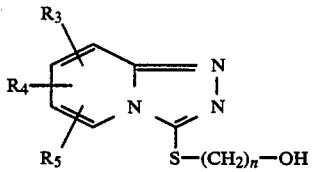

formula (VI)

in which $R_3$, $R_4$, $R_5$ and n are defined as above, which are themselves prepared by reacting halogenoalcohols with the compounds of the formula (II) under the same conditions as the halogenoalkylamines. The derivatives of the formula (IV) in which X' is a tosyloxy or mesyloxy group are obtained by reacting tosyl chloride or mesyl chloride with the derivatives of the formula (VI).

Some derivatives of the formula (I) in which $NR_1R_2$ forms a phenylpiperazine or heteroarylpiperazine can also be obtained by reacting a phenyl halide or a heteroaryl halide, in which the halogen is appropriately activated, with the corresponding NH piperazinyl derivative in a customary organic solvent, at between 50° and 150° C.

Some derivatives of the formula (II), for example the one in which $R_3=R_4=R_5=H$, are known in the literature (cf. BEILSTEIN, vol. 26, supplement II-page 86, compounds V and VI). The derivatives not described are prepared by methods which consist in reacting carbon disulfide with the hydrazino derivatives of the formula (VII):

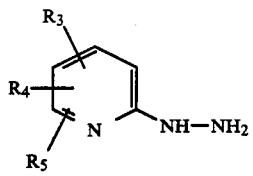

formula (VII)

in a solvent such as pyridine, at a temperature of between 20° and 120° C., $R_3$, $R_4$ and $R_5$ being defined as above. The 2-hydrazinopyridines of the formula (VII) are described in the literature (cf. BEILSTEIN, vol. 22, supplement I-page 688).

The derivatives of the formula (VII) which have not been described are synthesized by reacting hydrazine or hydrazine hydrate with the derivatives of the formula (VIII):

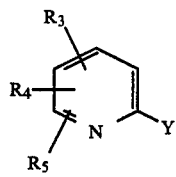

formula (VIII)

in a solvent such as an alcohol, or without a solvent, at a temperature of between 70° and 150° C. In the formula (VIII), $R_3$, $R_4$ and $R_5$ are defined as above, Y representing a halogen atom, in particular chlorine or bromine.

The compounds of the formula (III) are prepared by reacting thionyl chloride, tosyl chloride or mesyl chloride, by methods known per se, with alcohols of the formula (IX):

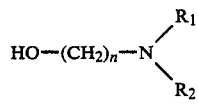

formula (IX)

in which $R_1$, $R_2$ and n are defined as above.

The alcohols of the formula (IX) can be prepared by reacting either ethylene oxide, in the case where n=2, or a halogenoalcohol with the corresponding amines of the formula (V) by methods known per se.

Some amines of the formula (V) are novel and make it possible to obtain particularly active derivatives of the formula (I), the said amines themselves having analgesic properties.

In particular, the Applicant Company claims the piperazine derivative of the formula (X):

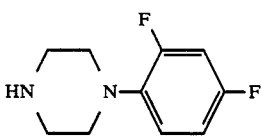

formula (X)

or one of its non-toxic acid addition salts.

2,4-Difluorophenylpiperazine (X) is obtained by reacting a bis-halogenoethylamine with 2,4-difluoroaniline in an aromatic solvent of the toluene or xylene type, or an alcohol, at a temperature of between 80° and 150° C.

The addition salts of the compounds of the formula (I) or the formula (X) can be obtained by reacting these compounds with a mineral or organic acid by a method known per se. Hydrochloric, hydrobromic, sulfuric, phosphoric, toluene-4-sulfonic, methanesulfonic, cyclohexylsulfamic, oxalic, succinic, formic, fumaric, maleic, citric, aspartic, cinnamic, lactic, glutamic, N-acetylaspartic, N-acetylglutamic, ascorbic, malic, benzoic, nicotine and acetic acids may be mentioned among the acids which can be used for this purpose.

According to the invention, therapeutic compositions are proposed which are especially useful for the treatment of pain. In addition, these derivatives possess valuable properties on the central nervous system, in particular non-sedative antianxiety properties which can be beneficial in the treatment of the psychic component of pain. Therefore, they are also claimed for these properties. The therapeutic compositions proposed contain at least one compound of the formula (I) or (X), or one of its non-toxic acid addition salts, in association with a physiologically acceptable excipient.

Further characteristics and advantages of the invention will be understood more clearly from the following description of some preparative examples; these in no way imply a limitation but are given by way of illustration.

Table III on pages 44–50 gives the structural formulae of some of the products.

EXAMPLE 1

4-(2,4-Difluorophenyl)piperazine dihydrochloride

Formula X

A mixture of 0.1 mol of bis-bromoethylamine hydrobromide and 0.1 mol of 2,4-difluoroaniline in 50 ml of butan-1-ol is heated at the boil for 14 hours. The reaction mixture is then cooled and the precipitate obtained is filtered off. The crystals are taken up with water and the mixture is rendered basic in the cold with a 10% solution of sodium hydroxide. The aqueous phase is extracted with chloroform and the extract is washed with water, dried over sodium carbonate and filtered. The chloroform is evaporated off and the residue obtained is taken up with acetone. Hydrogen chloride gas is bubbled through this solution, with stirring, until the pH is acid, and the crystals formed are allowed to settle. The crystals obtained are filtered off and then washed with acetone and dried. 4-(2,4-Difluorophenyl)piperazine dihydrochloride is thus recovered in the form of crystals melting at 205° C.

By calculating the quantity of hydrogen chloride gas added, it is also possible to prepare 4-(2,4-difluorophenyl)piperazine monohydrochloride, which melts at 182° C.

EXAMPLE 2

2-[4-(2,4-Difluorophenyl)piperazin-1-yl]ethanol

Formula IX: n=2,

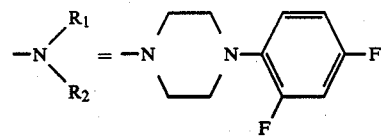

A solution of 72 g of 4-(2,4-difluorophenyl)piperazine and 50 g of 2-bromoethanol in 300 ml of xylene containing 55 ml of triethylamine is heated under reflux for 6 hours. The solution is then cooled and ether is added. The precipitate of triethylamine hydrobromide formed is filtered off and the filtrate is concentrated in vacuo. The residue obtained is then crystallized from an isopropyl ether/pentane mixture. The crystals are filtered off, washed with the same mixture and then dried. 60 g of 2-[4-(2,4-difluorophenyl)piperazin-1-yl]ethanol are thus recovered in the form of crystals melting at 54° C.

The following compounds were obtained by the procedure of Example 2:

EXAMPLE 3

2-[4-(2-Methylphenyl)-1,2,3,6-tetrahydropyridin-1-yl]ethanol

Formula IX: n=2,

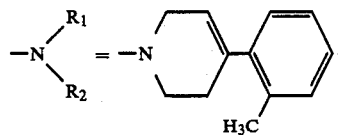

Form: oil.

EXAMPLE 4

2-[4-(3-Fluorophenyl)piperazin-1-yl]ethanol

Formula IX: n=2,

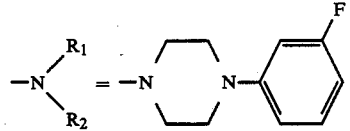

Form: crystals, m.p.=98° C.

EXAMPLE 5

2-[4-(2,5-Difluorophenyl)piperazin-1-yl]ethanol

Formula IX: n=2,

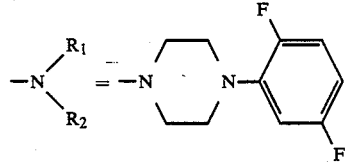

Form: oil.

EXAMPLE 6

3-[4-(2,4-Difluorophenyl)piperazin-1-yl]propanol

Formula IX: n=3,

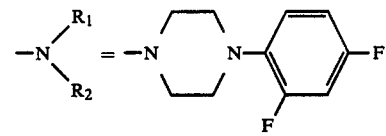

This compound is prepared by the procedure of Example 2 using 3-bromopropanol. 9.4 g of 4-(2,4-difluorophenyl)piperazine yielded 7.7 g of 3-[4-(2,4-difluorophenyl)piperazin-1-yl]propanol in the form of crystals melting at 88° C.

EXAMPLE 7

1-Chloro-2-[4-(2,4-difluorophenyl)piperazin-1-yl]ethane hydrochloride

Formula III: n=2,

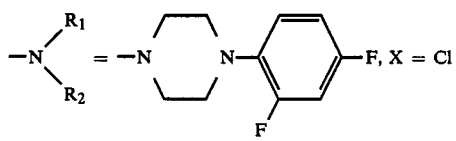

40 ml of thionyl chloride are added dropwise to a solution of 60 g of 2-[4-(2,4-difluorophenyl)piperazin-1-yl]ethanol, prepared in Example 2, in 300 ml of chloroform. When the addition is complete, the reaction mixture is heated under reflux for 5 hours. After return to room temperature, the crystals formed are filtered off, carefully washed with acetone and then dried to give 70 g of 1-chloro-2-[4-(2,4-difluorophenyl)piperazin-1-yl]ethane hydrochloride in the form of crystals melting at 218° C.

The following compounds were obtained by the procedure of Example 7:

EXAMPLE 8

1-Chloro-2-[4-(2-methylphenyl)-1,2,3,6-tetrahydropyridin-1-yl]ethane

Formula III: n=2,

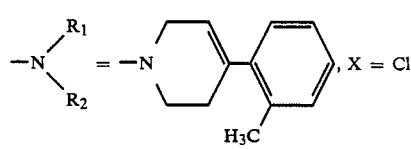

The base is freed from its hydrochloride. Form: oil.

EXAMPLE 9

1-Chloro-2-[4-(3-fluorophenyl)piperazin-1-yl]ethane dihydrochloride

Formula III: n=2,

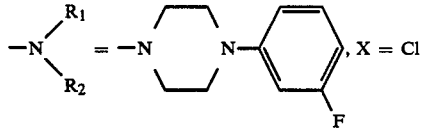

Form: crystals, m.p.=170°-2° C.

EXAMPLE 10

1-Chloro-2-[4-(2,5-difluorophenyl)piperazin-1-yl]ethane dihydrochloride

Formula III:

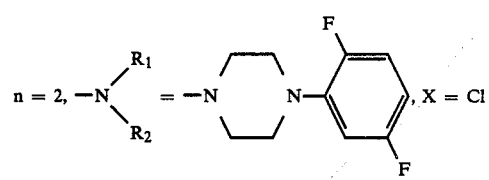

Form: hydrated crystals, m.p.=119°-21° C.

EXAMPLE 11

1-Chloro-3-[4-(2,4-difluorophenyl)piperazin-1-yl]propane hydrochloride

Formula III:

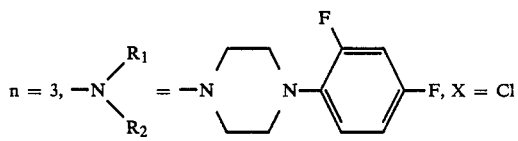

By following the procedure of Example 7, but starting from 7.7 g of 3-[4-(2,4-difluorophenyl)piperazin-1-yl]propanol prepared in Example 6, 8.7 g of 1-chloro-3-[4-(2,4-difluorophenyl)piperazin-1-yl]propane hydrochloride are obtained in the form of crystals melting at 174° C.

EXAMPLE 12

3-Trifluoromethyl-2-hydrazinopyridine

Formula VII: $R_3=3—CF_3$, $R_4=R_5=H$

A solution of 200 g of 2-chloro-3-trifluoromethylpyridine in 500 ml of ethanol and 300 ml of hydrazine hydrate is heated under reflux for 6 hours. The solution is then concentrated in vacuo and, after cooling, the crystalline residue is then taken up with water, filtered off, washed with water and dried to give 145 g of 3-trifluoromethyl-2-hydrazinopyridine in the form of crystals melting at 72° C.

EXAMPLE 13

3-Methyl-2-hydrazinoquinoline

Formula VII: $R_3=3-CH_3$, $R_4-R_5=5,6-CH=CH-CH=CH$ 73.5 g of 3-methyl-2-chloroquinoline in 102 ml of hydrazine hydrate are heated under reflux for 3 hours. The reaction mixture is cooled and the solid is filtered off, washed and dried. The crystalline mass obtained is recrystallized from isopropanol to give 50.5 g of 2-hydrazino-3-methylquinoline melting at 128° C.

The followiing compounds were obtained in an identical manner:

EXAMPLE 14

5-Chloro-2-hydrazinopyridine

Formula VII: $R_3=5-Cl$, $R_4=R_5=H$

Form: oil.

EXAMPLE 15

3-(α-Hydroxybenzyl)-2-hydrazinopyridine

Formula VII: $R_3=-CHOH-\phi$, $R_4=R_5=H$

Form: crystals melting at 132° C.

EXAMPLE 16

3-(1-Hydroxyethyl)-2-hydrazinopyridine

Formula VII: $R_3=CHOH-CH_3$, $R_4=R_5=H$

Form: oil.

EXAMPLE 17

3,5,7-Trimethyl-2-hydrazinoquinoline

Formula VII: $R_3=3-CH_3$, $R_4-R_5=$ $$5,6-\underset{CH_3}{C}=CH-\underset{CH_3}{C}=CH$$

Form: crystals melting at 117°-9° C.

EXAMPLE 18

3-Mercapto-8-trifluoromethyl-1,2,4-triazolo(4,3-a)pyridine

Formula II: $R_3=8-CF_3$, $R_4=R_5=H$ 16 ml of carbon disulfide are added dropwise at room temperature, with stirring, to a suspension of 40 g of 3-trifluoromethyl-2-hydrazinopyridine, prepared in Example 12, in 75 ml of pyridine. When the additioon is complete, stirring is continued for 15 minutes at room temperature and the reaction mixture is then heated under reflux for 5 hours. After cooling, the medium is concentrated in vacuo and water is then added. The solid residue obtained is filtered off, washed with water and dried to give 40 g of 3-mercapto-8-trifluoromethyl-1,2,4-triazolo(4,3-a)pyridine in the form of crystals melting at 236° C.

The following compounds were obtained in an identical manner:

EXAMPLE 19

3-Mercapto-6-chloro-1,2,4-triazolo(4,3-a)pyridine

Formula II: $R_3=6-Cl$, $R_4=R_5=H$

Form: crystals melting above 260° C.

EXAMPLE 20

3-Mercapto-8-(α-hydroxybenzyl)-1,2,4-triazolo(4,3-a)pyridine

Formula II: $R_3=8-(CHOH-\phi)$, $R_4=R_5=H$

Form: crystals melting at 220° C.

EXAMPLE 21

3-Mercapto-8-(1-hydroxyethyl)-1,2,4-triazolo(4,3-a)pyridine

Formula II: $R_3=8-(CHOH-CH_3)$, $R_4=R_5=H$

Form: oil.

EXAMPLE 22

1-Mercapto-4-methyl-s-triazolo(4,3-a)quinoline

Formula II: $R_3=8-CH_3$, $R_4-R_5=5,6-CH=CH-CH=CH-$ 17.5 ml of carbon disulfide are added dropwise at room temperature to a solution of 50.5 g of 3-methyl-2-hydriazinoquinoline, prepared in Example 13, in 365 ml of pyridine. The formation of a precipitate is observed, which redissolves gradually. When the addition is complete, the solution is heated for 1 h 15 min at 75° C. and then cooled the poured into a large volume of water. The precipitate is filtered off and washed with water. It is taken up in a hot dilute solution of sodium hydroxide, which is filtered. The filtrate is extracted with chloroform and then acidified with concentrated hydrochloric acid. The precipitate formed is filtered off, washed with water and dried to give 52 g of 1-mercapto-4-methyl-s-triazolo(4,3-a)quinoline melting at 268° C.

The following derivative was prepared by an identical method:

EXAMPLE 23

1-Mercapto-4,6,8-trimethyl-s-triazolo(4,3-a)quinoline

Formula II: $R_3=8-CH_3$, $R_4-R_5=$ $$6,5-CH=CH-\underset{CH_3}{C}=CH-\underset{CH_3}{}$$

Form: crystals melting above 260° C.

EXAMPLE 24

3-[2-(4-(3-Trifluoromethylphenyl)piperazin-1-yl)ethylmercapto]-8-trifluoromethyl-1,2,4-triazolo(4,3-a)pyridine maleate Formula I: $R_3=8-CF_3$, $R_4=R_5=H$, $n=2$, $$-N\begin{matrix}R_1\\R_2\end{matrix} = -N\diagdown N-\text{(3-CF}_3\text{-phenyl)}$$

A solution of 11 g of 3-mercapto-8-trifluoromethyl-1,2,4-triazolo(4,3-a)pyridine, prepared in Example 18, and 15 g of 1-chloro-2-[4-(3-trifluoromethylphenyl)piperazin-1-yl]ethane in 75 ml of ethanol containing 8 ml of triethylamine is heated under reflux for 6 hours. The reaction mixture is then concentrated in vacuo, water and ice are added and the extraction is carried out with ether. The organic phase is washed with water, with a dilute solution of sodium hydroxide and then again with water. The ether phase is dried and then concentrated and the residue obtained (21.5 g) is dissolved in acetone. A solution of 5.1 g of maleic acid in acetone is added to this acetone solution. The crystals which then form are filtered off, washed with acetone and ether and dried to give 11.5 g of 3-[2-(4-(3-trifluoromethylphenyl)piperazin-1-yl)ethylmercapto]-8-trifluoromethyl-1,2,4-triazolo(4,3-a)pyridine maleate in the form of crystals melting at 144°-5° C.

The following derivatives were obtained by this procedure, starting from the corresponding chlorine compounds and triazolopyridines:

EXAMPLE 25

3-[2-(4-Phenyl-1,2,3,6-tetrahydropyridin-1-yl)ethylmercapto]-8-trifluoromethyl-1,2,4-triazolo(4,3-a)pyridine maleate Formula I: $R_2=8-CF_3$, $R_4=R_5=H$, $n=2$,

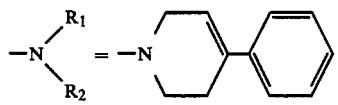

Form: crystals melting at 174° C.

EXAMPLE 26

3-[2-(4-(3-Trifluoromethylphenyl)piperazin-1-yl)ethylmercapto]-6-chloro-1,2,4-triazolo(4,3-a)pyridine hydrochloride Formula I: $R_3=6-Cl$, $R_4=R_5=H$, $n=2$,

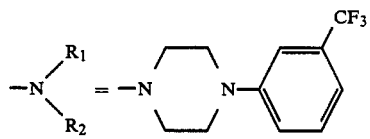

Form: crystals melting at 227° C.

EXAMPLE 27

3-[2-(4-(3-Trifluoromethylphenyl)piperazin-1-yl)ethylmercapto]-5-methyl-1,2,4triazolo(4,3-a)pyridine dihydrochloride Formula I: $R_3=5-CH_3$, $R_4=R_5=H$, $n=2$,

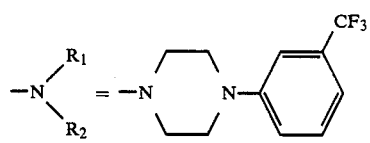

Form: crystals melting at 230° C.

EXAMPLE 28

3-[2-(4-(2,4-Difluorophenyl)piperazin-1-yl)ethylmercapto]-8-trifluoromethyl-1,2,4-triazolo(4,3-a)pyridine Formula I: $R_3=8-CF_3$, $R_4=R_5=H$, $n=2$,

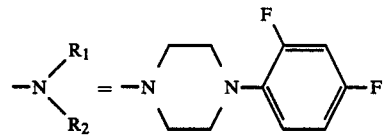

A solution of 13 g of 3-mercapto-8-trifluoromethyl-1,2,4-triazolo(4,3-a)pyridine, prepared in Example 18, and 15.5 g of 1-chloro-2-[4-(2,4-difluorophenyl)piperazin-1-yl]ethane as the base, freed from its hydrochloride, prepared in Example 7, by the addition of sodium hydroxide and extraction with ether, in 75 ml of ethanol containing 10 ml of triethylamine is heated under reflux for 6 hours. The reaction mixture is then concentrated in vacuo and the residue is taken up with methylene chloride, which is washed carefully with water, dried and then evaporated. The residue crystallizes when taken up in a mixture of ethyl ether and isopropyl ether. The crystals obtained are filtered off, washed with isopropyl ether and then dried to give 15.5 g of 3-[2-(4-(2,4-difluorophenyl)piperazin-1-yl)ethylmercapto]-8-trifluoromethyl-1,2,4-triazolo(4,3-a)pyridine in the form of crystals melting at 119°-120° C.

The following derivatives were obtained in an identical manner from the corresponding starting compounds:

EXAMPLE 29

3-[2-(4-(4-Fluorophenyl)-1,2,3,6-tetrahydropyridin-1-yl)ethylmercapto]-8-trifluoromethyl-1,2,4-triazolo(4,3-a)pyridine Formula I: $R_3=8-CF_3$, $R_4=R_5=H$, $n=2$,

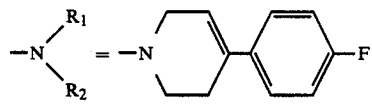

Form: crystals melting at 138°-9° C.

EXAMPLE 30

3-[2-(4-(4-Chlorophenyl)-1,2,3,6-tetrahydropyridin-1-yl)ethylmercapto]-8-trifluoromethyl-1,2,4-triazolo(4,3-a)pyridine Formula I: $R_3=8-CF_3$, $R_4=R_5H$, $n=2$,

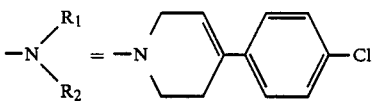

Form: crystals melting at 126°-7° C.

EXAMPLE 31

3-[2-(4-(3-Trifluoromethylphenyl)piperazin-1-yl)ethylmercapto]-6-methyl-1,2,4-triazolo(4,3-a)pyridine dihydrochloride Formula I: $R_3=6-CH_3$, $R_4=R_5=H$, $n=2$,

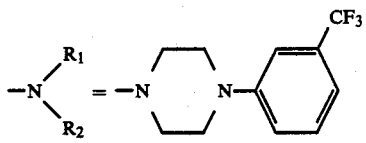

Form: crystals melting at 205°–6° C.

EXAMPLE 32

3-[3-(4-(2,4-Difluorophenyl)piperazin-1-yl)propylmercapto]-8-trifluoromethyl-1,2,4-triazolo(4,3-a)pyridine Formula I: $R_3=8-CF_3$, $R_4=R_5=H$, $n=3$,

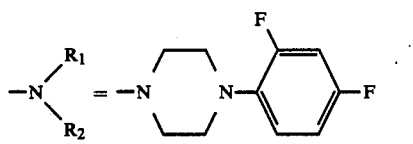

By following the procedure of Example 28, but using 14 g of 1-chloro-3-[4-(2,4-difluorophenyl)piperazin-1-yl]propane as the base, prepared in Example 11, and 11.8 g of 3-mecapto-8-trifluoromethyl-1,2,4-triazolo(4,3-a)pyridine, prepared in Example 18, 8 g of 3-[3-(4-(2,4-difluorophenyl)piperazin-1-yl)propylmercapto]-8-trifluoromethyl-1,2,4-triazolo(4,3-a)pyridine are obtained, after recrystallization from isopropyl ether, in the form of crystals melting at 88°–90° C.

EXAMPLE 33

3-[2-(4-(3-Trifluoromethylphenyl)piperazin-1-yl)ethylmercapto]-1,2,4-triazolo(4,3-a)pyridine maleate Formula I: $R_3=R_4=R_5=H$, $n=2$,

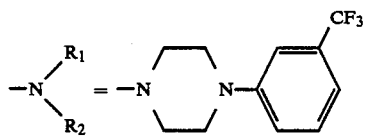

By following the procedure of Example 24, but using 6.6 g of 3-mercapto-1,2,4-triazolo(4,3-a)pyridine, 15 g of 3-[2-(4-(3-trifluoromethylphenyl)piperazin-1-yl)ethylmercapto]-1,2,4-triazolo(4,3-a)pyridine maleate are obtained, after recrystallization from ethanol, in the form of crystals melting at 136°–138° C.

The base crystallizes from ether and melts at 82° C.
The following derivatives were obtained in an analogous manner starting from the corresponding chlorine derivatives:

EXAMPLE 34

3-[2-(4-Phenyl-1,2,3,6-tetrahydropyridin-1-yl)ethylmercapto]-1,2,4-triazolo(4,3-a)pyridine dihydrochloride Formula I: $R_3=R_4=R_5=H$, $n=2$,

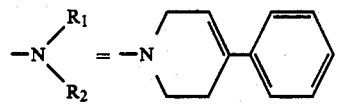

Form: crystals melting at 250°–4° C.

EXAMPLE 35

3-[2-(1,2,3,4-Tetrahydroisoquinolin-2-yl)ethylmercapto]-1,2,4-triazolo(4,3-a)pyridine dihydrochloride Formula I: $R_3=R_4=R_5=H$, $n=2$,

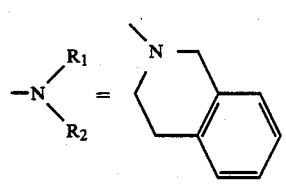

Form: crystals melting at 218°–220° C.

EXAMPLE 36

3-[2-(4-(2-Methoxyphenyl)piperazin-1-yl)ethylmercapto]-1,2,4-triazolo(4,3-a)pyridine trihydrochloride hydrate Formula I: $R_3=R_4=R_5=H$, $n=2$,

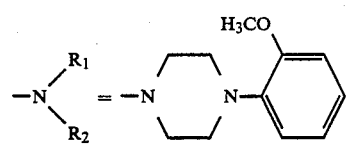

Form: crystals melting at 218° C.

EXAMPLE 37

3-[2-(4-(2-Methylphenyl)piperazin-1-yl)ethylmercapto]-1,2,4-triazolo(4,3-a)pyridine dihydrochloride Formula I: $R_3=R_4=R_5=H$, $n=2$,

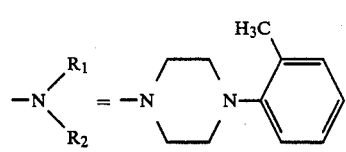

Form: crystals melting at 228° C.

EXAMPLE 38

3-[2-(4-(2,4-Difluorophenyl)piperazin-1-yl)ethylmercapto]-8-(1-hydroxyethyl)-1,2,4-triazolo(4,3-a)pyridine dihydrochloride hydrate Formula I: $R_3$=CHOH—$CH_3$, $R_4$=$R_5$=H, n=2,

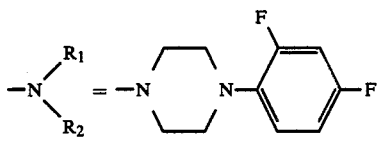

Form: crystals decomposing above 120° C.

EXAMPLE 39

3-[2-(4-(4-Fluorophenyl)piperazin-1-yl)ethylmercapto]-1,2,4-triazolo(4,3-a)pyridine trihydrochloride Formula I: $R_3$=$R_4$=$R_5$=H, n=2,

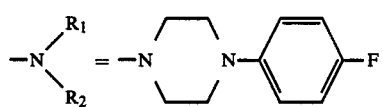

Form: crystals melting at 219°-220° C.

EXAMPLE 40

3-[2-(4-(2-Chlorophenyl)piperazin-1-yl)ethylmercapto]-1,2,4-triazolo(4,3-a)pyridine dihydrochloride Formula I: $R_3$=$R_4$=$R_5$=H, n=2,

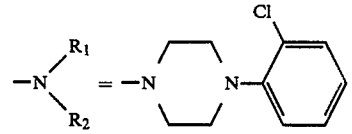

Form: crystals melting at 181°-2° C.

EXAMPLE 41

3-[2-(4-(2-Fluorophenyl)piperazin-1-yl) ethylmercapto]-1,2,4-triazolo(4,3-a)pyridine dihydrochloride Formula I: $R_3$=$R_4$=$R_5$=H, n=2,

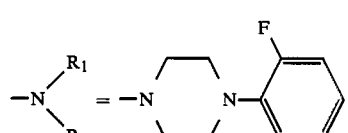

Form: crystals melting at 215° C.

EXAMPLE 42

3-[2-(4-(4-Methylphenyl)piperazin-1-yl)ethylmercapto]-1,2,4-triazolo(4,3-a)pyridine trihydrochloride Formula I: $R_3$=$R_4$=$R_5$=H, n=2,

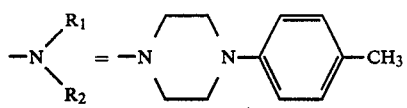

Form: crystals melting at 203° C.

EXAMPLE 43

3-[3-(4-(2,4-Difluorophenyl)piperazin-1-yl)propylmercapto]-1,2,4-triazolo(4,3-a)pyridine Formula I: $R_3$=$R_4$=$R_5$=H, n=3,

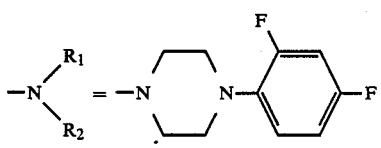

By following the procedure of Example 28, but using 7.7 g of 3-mercapto-1,2,4-triazolo(4,3-a)pyridine and 14 g of 1-chloro-3-[4-(2,4-difluorophenyl)piperazin-1-yl]propane, 7.5 g of 3-[3-(4-(2,4-difluorophenyl)piperazin-1-yl)propylmercapto]-1,2,4-triazolo(4,3-a)pyridine are obtained, after recrystallization from isopropyl ether, in the form of crystals melting at 77°-78° C.

EXAMPLE 44

3-[2-(4-(2,4-Difluorophenyl)piperazin-1-yl)ethylmercapto]-1,2,4-triazolo(4,3-a)pyridine Formula I: $R_3$=$R_4$=$R_5$=H, n=2,

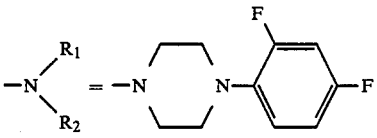

By following the procedure of Example 28, but starting from 9.3 g of 3-mercapto-1,2,4-triazolo(4,3-a)pyridine, 15 g of 3-[2-(4-(2,4-difluorophenyl)piperazin-1-yl)ethylmercapto]-1,2,4-triazolo(4,3-a)pyridine are prepared in the form of crystals melting at 98°-99° C.

The following compounds are obtained in an analogous manner, but starting from the corresponding chlorine derivatives:

EXAMPLE 45

3-[2-(4-(4-Fluorophenyl)-1,2,3,6-tetrahydropyridin-1-yl)ethylmercapto]-1,2,4-triazolo(4,3-a)pyridine Formula I: $R_3$=$R_4$=$R_5$=H, n=2,

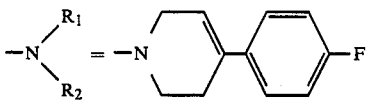

Form: crystals melting at 87°-9° C.

EXAMPLE 46

3-[2-(4-(2,4-Difluorophenyl)piperazin-1-yl)ethylmercapto]-8-(α-hydroxybenzyl)-1,2,4-triazolo(4,3-a)pyridine hydrate Formula I: $R_3$=CHOH—ϕ, $R_4$=$R_5$=H, n=2,

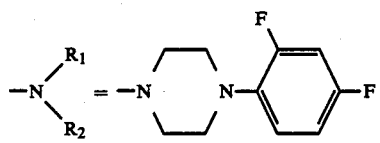

Form: crystals melting at 88° C.

EXAMPLE 47

3-[2-(4-(2-Methylphenyl)-1,2,3,6-tetrahydropyridin-1-yl)ethylmercapto]-1,2,4-triazolo(4,3-a)pyridine Formula I: $R_3$=$R_4$=$R_5$=H, n=2,

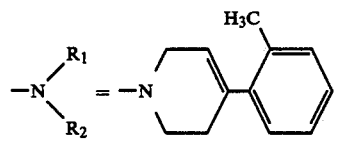

Form: crystals melting at 54° C.

EXAMPLE 48

3-[2-(4-(4-Chlorophenyl)-1,2,3,6-tetrahydropyridin-1-yl)ethylmercapto]-1,2,4-triazolo(4,3-a)pyridine Formula I: $R_3$=$R_4$=$R_5$=H, n=2,

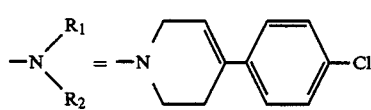

Form: crystals melting at 126°–7° C.

EXAMPLE 49

3-[2-(4-(3-Chlorophenyl)piperazin-1-yl)ethylmercapto]-1,2,4-triazolo(4,3-a)pyridine Formula I: $R_3$=$R_4$=$R_5$=H, n=2,

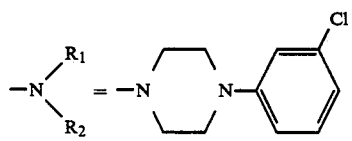

Form: crystals melting at 115°–6° C.
Maleate (ethanol), m.p.=132°–3° C.
Dihydrochloride (ethanol), m.p.=198°–9° C.

EXAMPLE 50

3-[2-(4-(4-Methoxyphenyl)piperazin-1-yl)ethylmercapto]-1,2,4-triazolo(4,3-a)pyridine Formula I: $R_3$=$R_4$=$R_5$=H, n=2,

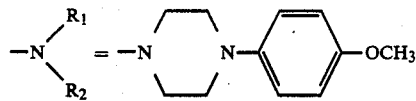

Form: crystals melting at 111° C.

EXAMPLE 51

3-[2-(4-(Diphenylmethyl)piperazin-1-yl)ethylmercapto]-1,2,4-triazolo(4,3-a)pyridine Formula I: $R_3$=$R_4$=$R_5$=H, n=2,

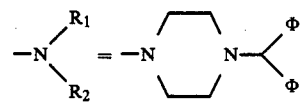

Form: crystals melting at 103° C.

EXAMPLE 52

3-[2-(4-(3-Fluorophenyl)piperazin-1-yl)ethylmercapto]-1,2,4-triazolo(4,3-a)pyridine Formula I: $R_3$=$R_4$=$R_5$=H, n=2,

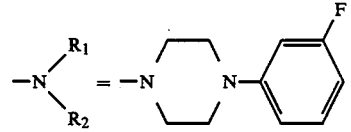

Form: crystals melting at 105°–6° C.

EXAMPLE 53

3-[2-(1,4-Dioxa-8-azaspiro(4,5)decan-8-yl)ethylmercapto]-1,2,4-triazolo(4,3-a)pyridine Formula I: $R_3$=$R_4$=$R_5$=H, n=2,

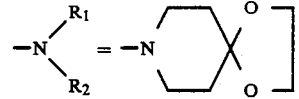

Form: crystals melting at 128° C.

EXAMPLE 54

3-[2-(4-Phenylpiperazin-1-yl)ethylmercapto]-1,2,4-triazolo(4,3-a)pyridine

Formula I: $R_3$=$R_4$=$R_5$=H, n=2,

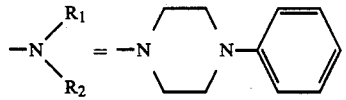

Form: crystals melting at 100°–1° C.

EXAMPLE 55

3-[(1-Benzoylpiperidin-4-yl)mercapto]-1,2,4-triazolo(4,3-a)pyridine

Formula I: $R_3=R_4=R_5=H$, $n=0$,

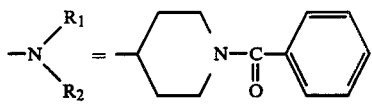

Form: crystals melting at 132°-3° C.

EXAMPLE 56

3-[2-(4-Oxopiperidin-1-yl)ethylmercapto]-1,2,4-triazolo(4,3-a)pyridine

Formula I: $R_3=R_4=R_5=H$, $n=2$,

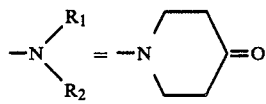

6.5 g of 3-[2-(1,4-dioxa-8-azaspiro(4,5)decan-8-yl)ethylmercapto]-1,2,4-triazolo(4,3-a)pyridine, prepared in Example 53, are heated under reflux for 10 hours in 200 ml of a 0.5N solution of hydrochloric acid. The reaction mixture is then cooled, rendered basic with a solution of sodium bicarbonate and extracted with chloroform. The chloroform phase is dried over magnesium sulfate and concentrated in vacuo. The residue obtained crystallizes from isopropyl acetate. The crystals are filtered off and dried to give 3.5 g of 3-[2-(4-oxopiperidin-1-yl)ethylmercapto]-1,2,4-triazolo(4,3-a)pyridine in the form of crystals melting at 76°-7° C.

EXAMPLE 57

1-[3-(4-(3-Trifluoromethylphenyl)piperazin1-yl)propylmercapto]-s-triazolo(4,3-a)quinoline Formula I: $R_3=H$,
$R_4-R_5=5,6-CH=CH-CH=CH-$, $n=3$,

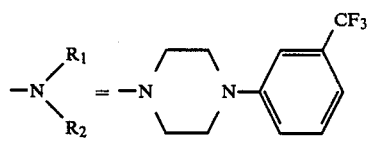

A suspension of 13.4 g of 1-mercapto-s-triazolo(4,3-a)quinoline, 20.5 g of 1-chloro-3-[4-(3-trifluoromethylphenyl)piperazin-1-yl]propane as the base and 11.2 ml of triethylamine in 150 ml of ethanol is heated under reflux for 7 hours. After cooling, the medium is concentrated in vacuo and the residue is then taken up in chloroform. The organic phase is washed with water, dried over sodium sulfate and then concentrated. The thick residue is crystallized by the addition of isopropyl ether, filtered off and dried. After recrystallization from ethanol, 12.7 g of 1-[3-(4-(3-trifluoromethylphenyl)piperazin-1-yl)propylmercapto]-s-triazolo(4,3-a)quinoline are obtained in the form of crystals melting at 117°-8° C.

EXAMPLE 58

1-[2-(4-(3-Trifluoromethylphenyl)piperazin-1-yl)ethylmercapto]-s-triazolo(4,3-a)quinoline Formula I: $R_3=H$,
$R_4-R_5=5,6-CH=CH-CH=CH-$, $n=2$,

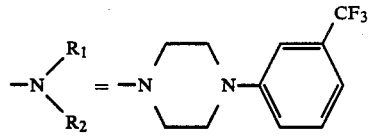

By following procedure of Example 57, starting from 21 g of 1-chloro-2-[4-(3-trifluoromethylphenyl)piperazin-1-yl]ethane as the base and 14.4 g of 1-mercapto-s-triazolo(4,3-a)quinoline, 13.5 g of 1-[2-(4-(3-trifluoromethylphenyl)piperazin-1-yl)ethylmercapto]s-triazolo(4,3-a)quinoline are obtained, after recrystallization from ethanol, in the form of crystals melting at 132° C.

EXAMPLE 59

1-[3-(4-(3-Trifluoromethylphenyl)piperazin-1-yl)propylmercapto]-4-methyl-s-triazolo(4,3-a)quinoline Formula I: $R_3=8-CH_3$,
$R_4-R_5=5,6-CH=CH-CH=CH-$, $n=3$,

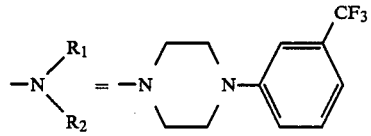

By following the procedure of Example 57, starting from 22 g of 1-chloro-3-[4-(3-trifluoromethylphenyl)-piperazin-1-yl]propane as the base and 15.4 g of 1-mercapto-4-methyl-s-triazolo(4,3-a)quinoline prepared in Example 22, 14 g of 1-[3-(4-(3-trifluoromethylphenyl)-piperazin-1-yl)propylmercapto]-4-methyl-s-triazolo(4,3-a)quinoline are obtained, after recrystallization from ethyl acetate, in the form of crystals melting at 137° C.

EXAMPLE 60

1-[2-(4-(2,4-Difluorophenyl)piperazin-1-yl)ethylmercapto]-4-methyl-s-triazolo(4,3-a)quinoline Formula I: $R_3=8-CH_3$,
$R_4-R_5=5,6-CH=CH-CH=CH-$, $n=2$,

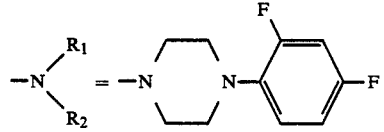

By following the procedure of Example 57, starting from 23 g of 1-chloro-2-[4-(2,4-difluorophenyl)piperazin-1-yl]ethane as the base, prepared from the hydrochloride of Example 7, and 19 g of 1-mercapto-4-methyl-s-triazolo(4,3-a)quinoline prepared in Example 22, 22 g of 1-[2-(4-(2,4-difluorophenyl)piperazin-1-yl)ethylmercapto]-4-methyl-s-triazolo(4,3-a)quinoline are obtained, after recrystallization from ethyl acetate, in the form of crystals melting at 124° C.

EXAMPLE 61

1-[2-(4-(2,4-Difluorophenyl)piperazin-1-yl)ethylmercapto]-s-triazolo(4,3-a)quinoline Formula I: $R_3$=H,
$R_4$-$R_5$=5,6—CH=CH—CH=CH—, n=2,

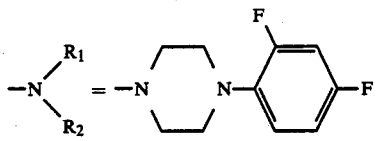

By following the procedure of Example 57, starting from 23 g of 1-chloro-2-[4-(2,4-difluorophenyl)piperazin-1-yl]ethane as the base, prepared from the hydrochloride of Example 7, and 17.8 g of 1-mercapto-s-triazolo(4,3-a)quinoline, 13.6 g of 1-[2-(4-(2,4-difluorophenyl)piperazin-1-yl)ethylmercapto]-s-triazolo(4,3-a)quinoline are obtained, after recrystallization from ethyl acetate, in the form of crystals melting at 114° C.

EXAMPLE 62

1-[2-(4-(2,4-Difluorophenyl)piperazin-1-yl)ethylmercapto]-5-methyl-s-triazolo(4,3-a)quinoline Formula I: $R_3$=7—CH$_3$,
$R_4$-$R_5$=5,6—CH=CH—CH=CH—, n=2,

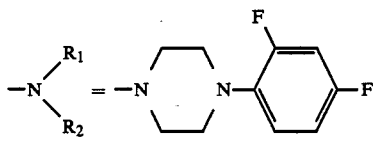

By following the procedure of Example 57, starting from 8.4 g of 1-chloro-2-[4-(2,4-difluorophenyl)piperazin-1-yl]ethane as the base, prepared from the hydrochloride of Example 7, and 7 g of 1-mercapto-5-methyl-s-triazolo(4,3-a)quinoline, 4.7 g of 1-[2-(4-(2,4-difluorophenyl)piperazin-1-yl)ethylmercapto]-5-methyl-s-triazolo(4,3-a)quinoline are obtained, after recrystallization from ethyl acetate, in the form of crystals melting at 133° C.

EXAMPLE 63

1-[2-(4-(3-Trifluoromethylphenyl)piperazin-1-yl)ethylmercapto]-4-methyl-s-triazolo(4,3-a)quinoline Formula I: $R_3$=8—CH$_3$,
$R_4$-$R_5$=5,6—CH=CH—CH=CH—, n=2,

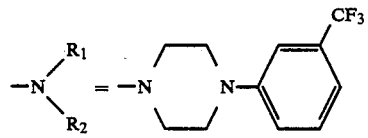

By following the procedure of Example 57, starting from 23.3 g of 1-chloro-2-[4-(3-trifluoromethylphenyl)-piperazin-1-yl]ethane as the base and 17.2 g of 1-mercapto-4-methyl-s-triazolo(4,3-a)quinoline prepared in Example 22, 16.5 g of 1-[2-(4-(3-trifluoromethylphenyl)-piperazin-1-yl)ethylmercapto]-4-methyl-s-triazolo(4,3-a)quinoline are obtained, after recrystallization from ethyl acetate, in the form of crystals melting at 120° C.

The following were obtained in an identical manner by the procedure of Example 57:

EXAMPLE 64

1-[2-(4-(4-Fluorophenyl)-1,2,3,6-tetrahydropyridin-1-yl)ethylmercapto]-s-triazolo(4,3-a)quinoline Formula I: $R_3$=H,
$R_4$-$R_5$=5,6—CH=CH—CH=CH—, n=2,

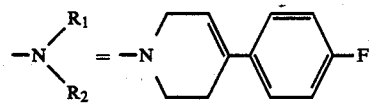

Form: crystals melting at 130° C.

EXAMPLE 65

1-[3-(4-(2,4-Difluorophenyl)piperazin-1-yl)propylmercapto]-s-triazolo(4,3-a)quinoline Formula I: $R_3$=H,
$R_4$-$R_5$=5,6—CH=CH—CH=CH—, n=3,

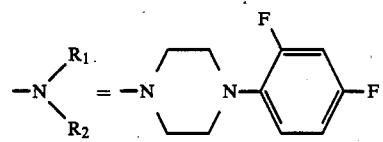

Form: crystals melting at 131°-3° C.

EXAMPLE 66

1-[3-(4-(2,4-Difluorophenyl)piperazin-1-yl)propylmercapto]-4-methyl-s-triazolo(4,3-a)quinoline Formula: $R_3$=8—CH$_3$,
$R_4$-$R_5$=5,6—CH=CH—CH=CH—, n=3,

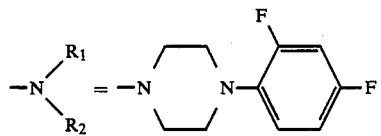

Form: crystals melting at 137°-8° C.

EXAMPLE 67

1-[3-(4-(2,4-Difluorophenyl)piperazin-1-yl)propylmercapto]-4,6,8-trimethyl-s-triazolo(4,3-a)quinoline Formula I: $R_3$=8—CH$_3$, $R_4$-$R_5$=

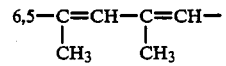

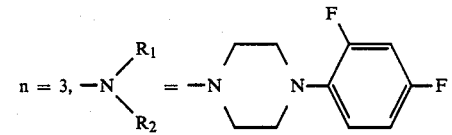

Form: crystals melting at 128°-130° C.

EXAMPLE 68

3-[2-(Methylamino)ethylmercapto]-1,2,4,-triazolo(4,3-a)pyridine hydrochloride

Formula I: $R_1=CH_3$, $R_2=R_3=R_4=R_5=H$, $n=2$

A solution of 18 g of N-methyl-2-chloroethylamine hydrochloride, 20 g of 3-mercapto-1,2,4-triazolo(4,3-a)pyridine and 40 ml of triethylamine in 150 ml of ethanol is heated under reflux for 2 hours. After evaporation, the residue is taken up in water, 0.1N sodium hydroxide is added and extraction is carried out with chloroform. The chloroform phase is washed with water, dried over sodium sulfate and evaporated to dryness. The residue obtained is dissolved in an ethyl ether/acetone mixture and the solution is acidified by the addition of a solution of ethyl ether saturated with hydrogen chloride gas. The precipitate formed is filtered off, washed with ether and dried to give 12.6 g of 3-[2-(methylamino)ethylmercapto]-1,2,4-triazolo(4,3-a)pyridine hydrochloride in the form of crystals melting at 195°–7° C.

The following compounds were synthesized by an identical procedure:

EXAMPLE 69

3-[2-(4-Morpholino)ethylmercapto]-1,2,4-triazolo(4,3-a)pyridine dihydrochloride

Formula I: $R_3=R_4=R_5=H$, $n=2$,

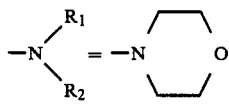

Form: crystals melting at 205°–210° C.

EXAMPLE 70

3-[(4-Benzylmorpholin-3-yl)methylmercapto]1,2,4-triazolo(4,3-a)pyridine maleate

Formula I: $R_3=R_4=R_5=H$, $n=1$,

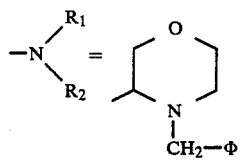

Form: crystals melting at 159°–160° C.

EXAMPLE 71

3-[(4-Benzylmorpholin-2-yl)methylmercapto]1,2,4-triazolo(4,3-a)pyridine dihydrochloride Formula I: $R_3=R_4=R_5=H$, $n=1$,

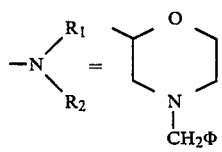

Form: crystals melting at 203°–205° C.

EXAMPLE 72

2-[1,2,4-Triazolo(4,3-a)pyridin-3-ylmercapto]ethanol

Formula VI: $R_3=R_4=R_5=H$, $n=2$ 60 g of 3-mercapto-1,2,4-triazolo(4,3-a)pyridine are dissolved in 500 ml of ethanol. 21 g of sodium carbonate and 29 ml of 2-bromoethanol are then added. The reaction mixture is heated under reflux for 9 hours, the mineral substances are filtered off, the filtrate is then concentrated in vacuo, the concentrate is taken up with water acidified with 0.5N hydrochloric acid and extraction is carried out with chloroform. The aqueous phase is then rendered basic with aqueous ammonia, saturated with sodium chloride and then extracted with chloroform. The chloroform phase obtained is dried over magnesium sulfate and then concentrated in vacuo. The crystals which then form are taken up with pentane, filtered off, washed with pentane and dried to give 69.2 g of 2-[1,2,4-triazolo(4,3-a)pyridin-3-ylmercapto]ethanol in the form of crystals melting at 84° C.

EXAMPLE 73

1-Chloro-2-[1,2,4-triazolo(4,3-a)pyridin-3-ylmercapto]ethane

Formula IV: $R_3=R_4=R_5=H$, $X'=Cl$ 53.7 ml of thionyl chloride are added dropwise to a solution of 57.9 g of 2-[1,2,4-triazolo(4,3-a)pyridin-3-ylmercapto]ethanol, prepared in Example 72, in 400 ml of chloroform. The reaction medium is heated under reflux for 4 hours and then cooled. The crystals formed are filtered off, washed with chloroform and then taken up with water. The aqueous phase is rendered basic with aqueous ammonia and then extracted with chloroform. The chloroform phase is dried over sodium sulfate and concentrated in vacuo. The residue obtained crystallizes. 46.8 g of 1-chloro-2-[1,2,4-triazolo(4,3-a)pyridin-3-ylmercapto]ethane are thus recovered in the form of crystals melting at 94° C.

EXAMPLE 74

3-[2-(4-(3-Cyanopyridin-2-yl)piperazin-1-yl)ethylmercapto]-1,2,4-triazolo(4,3-a)pyridine Formula I: $R_3=R_4=R_5=H$, $n=2$,

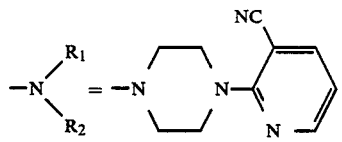

A solution of 13 g of 1-chloro-2-[1,2,4-triazolo(4,3-a)pyridin-3-ylmercapto]ethane, prepared in Example 73, and 11.5 g of (3-cyanopyridin-2-yl)piperazine in 200 ml of xylene containing 0.5 g of sodium iodide and 8.5 ml of triethylamine is heated under reflux for 7 hours. The reaction medium is then cooled and the xylene phase is washed with water and then extracted with a dilute solution of hydrochloric acid. The aqueous phase is extracted with chloroform and then rendered basic in the cold with an aqueous solution of ammonia. The basic products are then extracted with chloroform, which is washed with water, dried over magnesium sulfate and concentrated in vacuo. The residue obtained is filtered on silica gel (eluent: chloroform/methanol 98/2) to give an oil which crystallizes from ethyl ether.

The crystals are filtered off and dried and 5.5 g of 3-[2-(4-(3-cyanopyridin-2-yl)piperazin-1-yl)ethylmercapto]-1,2,4-triazolo(4,3-a)pyridine melting at 116°-7° C. are recovered.

The following compounds were obtained by this procedure:

EXAMPLE 75

3-[2-(4-(3-Methoxyphenyl)piperazin-1-yl)ethylmercapto]-1,2,4-triazolo(4,3-a)pyridine Formula I: R$_3$=R$_4$=R$_5$=H, n=2,

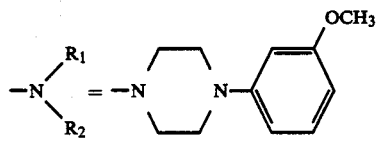

Form: crystals melting at 105° C.

EXAMPLE 76

3-[2-(4-(3,4-Dichlorophenyl)piperazin-1-yl)ethylmercapto]-1,2,4-triazolo(4,3-a)pyridine Formula I: R$_3$=R$_4$=R$_5$=H, n=2,

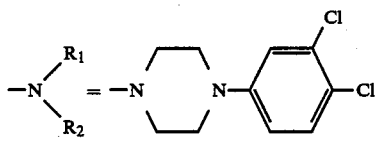

Form: crystals melting at 122°-3° C.

EXAMPLE 77

3-[2-(4-(3-Hydroxyphenyl)piperazin-1-yl)ethylmercapto]-1,2,4-triazolo(4,3-a)pyridine Formula I: R$_3$=R$_4$=R$_5$=H, n=2,

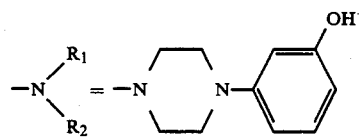

Form: crystals melting at 152° C.

EXAMPLE 78

3-[2-(4-(4-Methylphenylsulfonyl)piperazin-1-yl)ethylmercapto]-1,2,4-triazolo(4,3-a)pyridine Formula I: R$_3$=R$_4$=R$_5$=H, n=2,

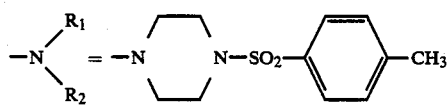

30 g of postassium carbonate are added to a solution of 32.7 g of 3-mercapto-1,2,4-triazolo(4,3-a)pyridine in 300 ml of ethanol and the mixture is heated to the reflux temperature. After 15 minutes, a solution of 65.5 g of 1-chloro-2-[4-(4-methylphenylsulfonyl)piperazin-1-yl]ethane in 100 ml of ethanol is added and refluxing is continued for 3 hours. The reaction mixture is then cooled, the mineral substances are filtered off and the filtrate is concentrated in vacuo. The residue is taken up with chloroform, which is washed with water, and the chloroform phase is then extracted with a 0.5N solution of hydrochloric acid. The acidic aqueous phase is then rendered basic in the cold with a 0.5N aqueous solution of sodium hydroxide and then extracted with chloroform. The chloroform phase is washed with water, dried over sodium sulfate and then concentrated in vacuo to give 73 g of 3-[2-(4-(4-methylphenylsulfonyl)piperazin-1-yl)ethylmercapto]1,2,4-triazolo(4,3-a)pyridine in the form of a thick oil, which is used in the crude state for the next step.

EXAMPLE 79

3-[2-(Piperazin-1-yl)ethylmercapto]-1,2,4-triazolo(4,3-a)pyridine

Formula I: R$_3$=R$_4$=R$_5$=H, n=2,

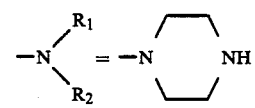

73 g of 3-[2-(4-(4-methylphenylsulfonyl)piperazin-1-yl)ethylmercapto]-1,2,4-triazolo(4,3-a)pyridine, prepared in Example 78, are dissolved in 360 ml of a concentrated solution of hydrochloric acid and the resulting solution is heated under reflux for 8 hours. After cooling, it is neutralized with sodium hydroxide and extracted with chloroform. The chloroform phase is dried over magnesium sulfate and concentrated in vacuo to give 37.4 g of 3-[2-(piperazin-1-yl)ethylmercapto]1,2,4-triazolo(4,3-a)pyridine in the form of an oil which crystallizes from acetone. M.p.=104° C.

EXAMPLE 80

3-[2-(4-(Pyrimidin-2-yl)piperazin-1-yl)ethylmercapto]-1,2,4-triazolo(4,3-a)pyridine Formula I: R$_3$=R$_4$=R$_5$=H, n=2,

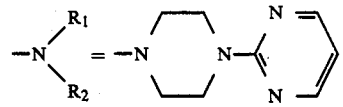

4.8 g of 3-[2-(piperazin-1-yl)ethylmercapto]1,2,4-triazolo(4,3-a)pyridine, prepared in Example 79, and 2.1 g of 2-chloropyrimidine are heated under reflux in 140 ml of isopropanol in the presence of 2.5 g of potassium carbonate. After heating for 2 hours, the medium is cooled, the mineral substances are filtered off and the filtrate is concentrated. The oily residue is filtered on silica gel (eluent: chloroform/methanol 90/10). The resulting residue crystallizes from an ethyl ether/isopropyl ether mixture to give 2.8 g of 3-[2-(4-(pyrimidin-2-yl)piperazin-1-yl)ethylmercapto]1,2,4-triazolo(4,3-a)pyridine in the form of crystals melting at 126°-7° C.

The following compounds were obtained by this procedure:

EXAMPLE 81

3-[2-(4-(3-Trifluoromethylpyridin-2-yl)piperazin-1-yl)e-
thylmercapto]-1,2,4-triazolo(4,3-a)pyridine Formula I: $R_3=R_4=R_5=H$, n=2,

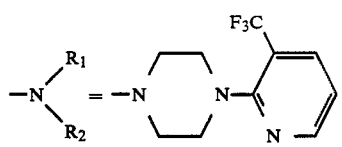

Form: crystals melting at 67°-8° C.

EXAMPLE 82

3-[2-(4-(4-Trichloromethylpyrimidin-2-yl)piperazin-1-
yl)ethylmercapto]-1,2,4-triazolo(4,3-a)pyridine Formula I: $R_3=R_4=R_5=H$, n=2,

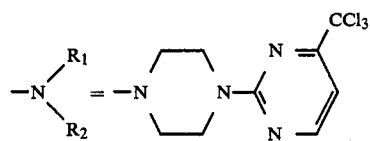

Form: crystals melting at 132° C.

EXAMPLE 83

3-[2-(4-(5-Cyanopyridin-2-yl)piperazin-1-yl)ethylmer-
capto]-1,2,4-triazolo(4,3-a)pyridine Formula I: $R_3=R_4=R_5=H$, n=2,

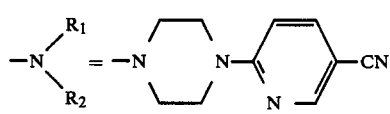

Form: crystals melting at 134° C.

EXAMPLE 84

3-[2-(4-(4-Methylpyrimidin-2-yl)piperazin1-yl)ethyl-
mercapto]-1,2,4-triazolo(4,3-a)pyridine Formula I: $R_3=R_4=R_5=H$, n=2,

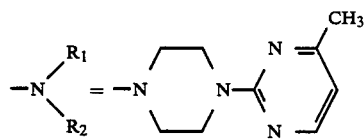

Form: crystals melting at 129° C.

EXAMPLE 85

3-[2-(4-(3-Nitropyridin-2-yl)piperazin-1-yl)ethylmer-
capto]-1,2,4-triazolo(4,3-a)pyridine Formula I: $R_3=R_4=R_5=H$, n=2,

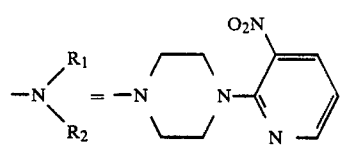

Form: crystals melting at 166° C.

EXAMPLE 86

3-[2-(4-(3-Aminopyridin-2-yl)piperazin-1-yl)ethylmer-
capto]-1,2,4-triazolo(4,3-a)pyridine Formula I: $R_3=R_4=R_5=H$, n=2,

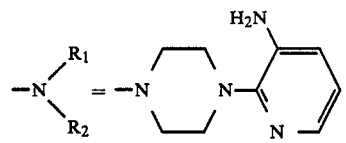

3 g of 3-[2-(4-(3-nitropyridin-2-yl)piperazin-1-yl)e-
thylmercapto]-1,2,4-triazolo(4,3-a)pyridine, prepared in
Example 85, are dissolved in 50 ml of ethanol and hy-
drogenated at room temperature and normal pressure in
the presence of Raney Ni. When the theoretical quan-
tity of hydrogen has been absorbed, the nickel is filtered
off and the filtrate is concentrated in vacuo. The residue
is filtered on silica gel (eluent: chloroform/methanol
96/4). The residue recovered crystallizes from isopro-
pyl ether. 1.8 g of crystals of 3-[2-(4-(3-aminopyridin-2-
yl)piperazin-1-yl)ethylmercapto]-1,2,4-triazolo(4,3-
a)pyridine melting at 104° C. are thus recovered.

EXAMPLE 87

3-[(Piperidin-4-yl)mercapto]-1,3,4-triazolo(4,3-a)pyri-
dine maleate

Formula I: $R_3=R_4=R_5=H$, n=0,

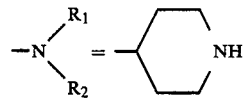

A solution of 6.3 g of 3-[(1-benzoylpiperidin-4-
yl)mercapto]-1,2,4-triazole(4,3-a)pyridine, prepared in
Example 55, in 60 ml of a 1.55N solution of hydrochlo-
ric acid is heated under reflux for 7 hours. After cool-
ing, the benzoic acid formed is filtered off and the fil-
trate is extracted with chloroform and then concen-
trated to half its volume. The aqueous solution is ren-
dered basic with sodium carbonate and then extracted
with chloroform. The organic phase is dried and then
concentrated to give 4.5 g of oil.

This oil is taken up in acetone and treated with a
solution of 2.3 g of maleic acid in acetone.

This gives 3.3 g of 3-[(piperidin-4-yl)mercapto]-1,2,4-
triazolo(4,3-a)pyridine maleate in the form of crystals
melting at 150°-1° C.

EXAMPLE 88

3-[2-(4-(2,5-Difluorophenyl)piperazin-1-yl)ethylmer-
capto]-1,2,4-triazolo(4,3-a)pyridine Formula I: $R_3=R_4=R_5=H$, n=2,

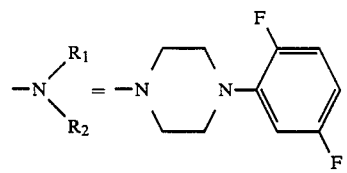

By following the procedure of Example 28, but starting from 7.5 g of 3-mercapto-1,2,4-triazolo(4,3-a)pyridine and 12.9 g of 1-chloro-2-[4-(2,5-difluorophenyl)-piperazin-1-yl]ethane as the base, obtained from the dihydrochloride prepared in Example 10, 3.3 g of 3-[2-(4-(2,5-difluorophenyl)piperazin-1-yl)ethylmercapto]-1,2,4-triazolo(4,3-a)pyridine are obtained in the form of crystals melting at 83°–84° C.

PHARMACOLOGY

*Principle

The analgesic activity of the products of the examples claimed in the present Application was evaluated according to two methodologies:

the method of Siegmund et al. (1), in which the pain reaction is caused by phenylbenzoquinone. This method makes it possible to assess the analgesic activity of molecules having both a peripheral and a central action.

the hot plate method described by Eddy et al. (2). This method is more specific for molecules possessing an analgesic activity of central origin.

*Materials

Animals

Male mice of the $CD_1$ strain (Charles River) and $OF_1$ strain (Iffa Credo), weighing from 19 to 22 g, were used for the Siegmund test and the Eddy test respectively. The tests were carried out at an ambient temperature of $21° \pm 2°$ C.

Products (examples claimed)

The products were suspended in an aqueous mixture of 1% gum arabic, 0.1% sodium chloride and 0.001% Tween 80.

The animals in the control groups received the vehicle.

*Methods

Siegmund test with phenylbenzoquinone

Procedure

One hour after administration of the product studied, 0.20 to 0.22 ml of a 0.02% aqueous-alcoholic solution of phenylbenzoquinone is administered to the mice intraperitoneally.

The number of pain reactions (twists and stretches) is counted from the 5th to the 10th minute.

Schedule of administration

The products of the examples studied were administered to groups of 6 to 12 mice by gastric intubation (0.5 ml/20 g), one hour before phenylbenzoquinone, according to the following dosage schedule:

0, 0.3, 1, 3, 10, 30, 100 mg.kg$^{-1}$.

Expression of the results

The percentage inhibition of pain manifestations was calculated from the mean numbers of twists per group.

Hot plate test (Eddy)

Procedure

The mice are placed on a thermostatically controlled metal plate at 56° C. The reaction time of the animals, represented by licking of the front paws, is measured. In no case are the mice left in contact with the hot plate for more than 30 seconds.

Schedule of administration

The products of the examples studied are administered to groups of 10 mice intraperitoneally (0.5 ml/20 g), 30 minutes before they are placed on the plate. These products are administered according to the following dosage schedule:

0, 3, 10, 30, 100 mg.kg$^{-1}$.

Expression of the results

The difference between the maximum reaction time (30 seconds) and the mean of the reaction times for each of the treated groups was calculated.

*Statistics

The 50% active doses and their confidence limits were determined from the linear regression carried out on the parameters measured.

*Results

The $AD_{50}$ values obtained for the two tests used are collated in Tables I and II.

*Toxicity

Preliminary toxicity studies carried out by oral administration to rats made it possible to show that the majority of the products of the examples claimed were well tolerated at doses <300 mg.kg$^{-1}$.

TABLE 1

Analgesic activity of the products of the examples claimed in the Siegmund test with phenylbenzoquinone after oral administration

| Product of Example | Number of animals per group | $AD_{50}$ confidence limits (mg · kg$^{-1}$) |
|---|---|---|
| 1 | 12 | 2.16 (1.28–3.66) |
| 24 | 12 | 4.53 (2.60–7.90) |
| 28 | 12 | 22.37 (16.05–31.19) |
| 31 | 6 | 3.60 (1.26–10.32) |
| 32 | 12 | 12.57 (9.05–17.46) |
| 33 | 12 | 1.71 (1.00–2.92) |
| 41 | 6 | 3.19 (1.38–7.34) |
| 43 | 6 | 13.87 (10.38–18.52) |
| 44 | 6 | 10.98 (7.21–16.70) |
| 45 | 6 | 33.02 (23.97–45.5) |
| 48 | 6 | 16.10 (9.71–26.67) |
| 49 | 6 | /2.45 (1.06–5.66) |
| 57 | 6 | 8.56 (2.15–34) |
| 59 | 6 | 14.12 (6.11–32.64) |
| 62 | 6 | 11.02 (3.99–30.41) |
| 63 | 6 | 8.17 (5.28–12.64) |
| 66 | 6 | 17.85 (14.01–22.75) |

Bibiographic references (1) Siegmund E., Cadmus R., Lu G. A method for evaluating both non-narcotic and narcotic analgesics. Proc. Soc. Exp. Biol. Med., 1957, 95, 729–731.

(2) Eddy N. B., Touchberry C. F., Lieberman J. E. Synthetic analgesics: 1—Methadone isomers and derivatives. J. Pharmacol. Exp. Ther., 1950, 98, 121–137.

TABLE III
| Code | Formula | Example | Code | Formula | Example |
|------|---------|---------|------|---------|---------|
| 5221-01 | 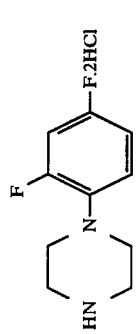 | 1 | 26-26 |  | 27 |
| | | | 5222-02 | 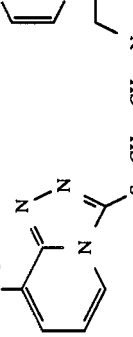 | 28 |
| 5222-01 | 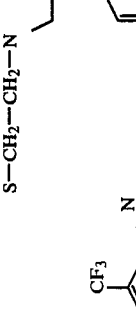 | 24 | 26-10 | 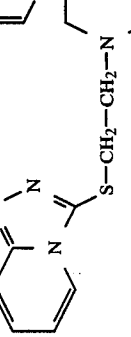 | 29 |
| 26-4 | 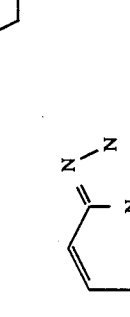 | 25 | 26-19 | 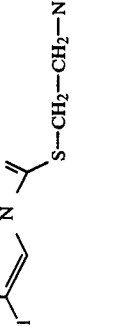 | 30 |
| 26-25 |  | 26 | 26-27 |  | 31 |

TABLE III-continued

| Code | Formula | Example | Code | Formula | Example |
|---|---|---|---|---|---|
| 5222-03 | [structure with CF₃ on pyridine, S-CH₂-CH₂-CH₂-N-piperazine-N-(2,4-difluorophenyl)] | 32 | 26-29 | [structure: pyridine-S-CH₂-CH₂-N-piperazine-N-(2-methylphenyl), 2HCl] | 37 |
| 5222-04 | [structure: pyridine-S-CH₂-CH₂-N-piperazine-N-(3-CF₃-phenyl), maleate (COOH-CH=CH-COOH)] | 33 | 26-16 | [structure: 3-(CHOH-CH₃)-pyridine-S-CH₂-CH₂-N-piperazine-N-(2,4-difluorophenyl), 2HCl, H₂O] | 38 |
| 26-13 | [structure: pyridine-S-CH₂-CH₂-N-tetrahydropyridine-phenyl, 2HCl] | 34 | 26-31 | [structure: pyridine-S-CH₂-CH₂-N-piperazine-N-(4-fluorophenyl), 3HCl] | 39 |
| 26-24 | [structure: pyridine-S-CH₂-CH₂-N-tetrahydroisoquinoline, 2HCl] | 35 | 26-32 | [structure: pyridine-S-CH₂-CH₂-N-piperazine-N-(2-chlorophenyl), 2HCl] | 40 |
| 26-28 | [structure: pyridine-S-CH₂-CH₂-N-piperazine-N-(2-methoxyphenyl), 3HCl, H₂O] | 36 | 26-34 | [structure: pyridine-S-CH₂-CH₂-N-piperazine-N-(2-fluorophenyl), 2HCl] | 41 |

TABLE III-continued
| Code | Formula | Example | Code | Formula | Example |
|---|---|---|---|---|---|
| 26-35 |  3HCl | 42 | 26-17 | 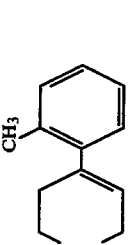 | 47 |
| 5222-05 | 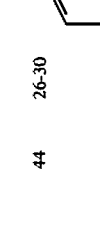 | 43 | 26-18 |  | 48 |
| 5222-06 |  | 44 | 26-30 | 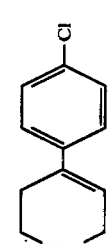 2HCl | 49 |
| 26-12 |  | 45 | 26-39 |  | 50 |
| 26-14 | 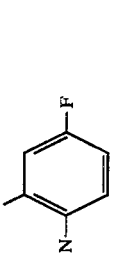 H₂O | 46 | 26-46 | 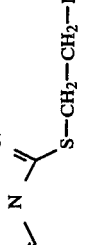 | 51 |

TABLE III-continued

| Code | Formula | Example | Code | Formula | Example |
|------|---------|---------|------|---------|---------|
| 26-49 | 3-F-C6H4-piperazine-CH2CH2-S-pyridyl-N=N | | 26-3 | 3-CF3-C6H4-piperazine-CH2CH2-S-quinolinyl-N=N | 58 |
| 26-51 | C6H5-piperazine-CH2CH2-S-pyridyl-N=N | 52 | 26-5 | 3-CF3-C6H4-piperazine-CH2CH2CH2-S-(2-CH3-quinolinyl)-N=N | 59 |
| 26-52 | C6H5-C(=O)-piperidine-S-pyridyl-N=N | 54 | 26-6 | 2,4-F2-C6H3-piperazine-CH2CH2-S-(3-CH3-quinolinyl)-N=N | 60 |
| 26-50 | (4-oxo-piperidine)-CH2CH2-S-pyridyl-N=N | 55 | 26-7 | 2,4-F2-C6H3-piperazine-CH2CH2-S-quinolinyl-N=N | 61 |
| 26-2 | 3-CF3-C6H4-piperazine-CH2CH2-S-quinolinyl-N=N | 56 | 26-8 | 2,4-F2-C6H3-piperazine-CH2CH2-S-(CH3-substituted quinolinyl)-N=N | 62 |

TABLE III-continued

| Code | Formula | Example | Code | Formula | Example |
|---|---|---|---|---|---|
| 26-9 | (3-CF₃-phenyl-piperazinyl-CH₂CH₂-S- quinoline with CH₃) | 63 | 26-15 | (pyrazolo-pyridine-S-CH₂CH₂-NH-CH₃) · HCl | 68 |
| 26-11 | (4-F-phenyl-tetrahydropyridinyl-CH₂CH₂-S- quinoline) | 64 | 8039-01 | (pyrazolo-pyridine-S-CH₂CH₂-morpholine) · 2HCl | 69 |
| 26-21 | (2,4-diF-phenyl-piperazinyl-CH₂CH₂CH₂-S- quinoline) | 65 | 26-1 | (pyrazolo-pyridine-S-CH₂-(3-CH₂φ-morpholine)) · maleate (COOH-CH=CH-COOH) | 70 |
| 26-22 | (2,4-diF-phenyl-piperazinyl-CH₂CH₂CH₂-S- quinoline with CH₃) | 66 | 26-20 | (pyrazolo-pyridine-S-CH₂-(2-CH₂φ-morpholine)) · 2HCl | 71 |

TABLE III-continued

| Code | Formula | Example | Code | Formula | Example |
|------|---------|---------|------|---------|---------|
| 26-23 | (structure with CH₃, CH₃, CH₃ substituted quinoline, S–CH₂–CH₂–CH₂–N piperazine, 2,4-difluorophenyl) | 67 | 26-33 | (pyridinyl-thio-CH₂CH₂-piperazine-pyridyl with CN) | 74 |
| 26-38 | (OCH₃-phenyl piperazine, S–CH₂–CH₂–) | 75 | 26-43 | (CCl₃ pyrimidine, piperazine) | 82 |
| 26-37 | (Cl, Cl dichlorophenyl piperazine) | 76 | 26-44 | (CN pyridyl piperazine) | 83 |
| 26-41 | (OH phenyl piperazine) | 77 | 26-45 | (CH₃ pyrimidine piperazine) | 84 |
| 26-42 | (pyrimidinyl piperazine) | 80 | 26-47 | (NO₂ pyridyl piperazine) | 85 |

TABLE III-continued

| Code | Formula | Example | Code | Formula | Example |
|---|---|---|---|---|---|
| 26-36 | (structure with triazolopyridine-S-CH₂-CH₂-piperazine-pyridine with CF₃) | 81 | 26-48 | (structure with triazolopyridine-S-CH₂-CH₂-piperazine-pyridine with NH₂) | 86 |
| 26-53 | (structure with triazolopyridine-S-piperidine-NH, with maleic acid COOH/COOH) | 87 | | | |
| 26-55 | (structure with triazolopyridine-S-CH₂-CH₂-piperazine-2,5-difluorophenyl) | 88 | | | |

What is claimed is:

1. A compound having the formula:

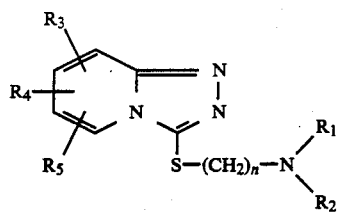

wherein n is an integer from 1 to 8 inclusive;
NR₁R₂ is 4-(3-trifluoromethylphenyl) piperazine-1-yl;
and each of R₃, R₄, R₅ is hydrogen, lower alkyl, hydroxyalkyl, a hydroxybenzyl group, a halogen, a trifluoromethyl, methoxy, thiomethyl, a nitro, or two of them together form a phenyl ring;
and the non-toxic acid addition salts.

2. A compound having the formula:

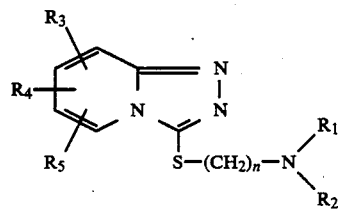

wherein n is an integer of from 1 to 8;
NR₁R₂ is 4(2,4-difluorophenyl)piperazine-1-yl;
and each of R₃, R₄, R₅ is hydrogen, lower alkyl, hydroxyalkyl, hydroxybenzyl group, halogen, trifluoromethyl, methoxy, thiomethyl, nitro, or two of them together form a phenyl ring
and the non-toxic acid addition salts.

3. A compound having the formula:

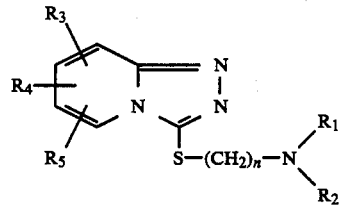

wherein n is an integer from 1 to 8 inclusive;
NR₁R₂ is 4-(3-chlorophenyl)piperazine-1-yl;
and each of R₃, R₄, R₅ is hydrogen, a lower alkyl, a hydroxyalkyl, a hydroxybenzyl group, a halogen, a trifluoromethyl, a methoxy, a thiomethyl, a nitro, or two of them together form a phenyl ring
and the non-toxic acid addition salts.

4. A compound having a formula:

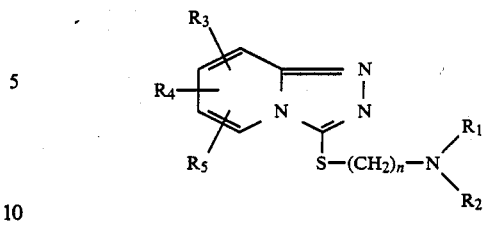

wherein n is an integer from 1 to 8 inclusive;
NR₁R is 4-(2-fluorophenyl)piperazine-1-yl;
and each of R₃, R₄, R₅ is hydrogen, lower alkyl, hydroxyalkyl, hydroxybenzyl group, halogen, trifluoromethyl, methoxy, thiomethyl, nitro, or two of them together form a phenyl ring,
and the non-toxic acid addition salts.

5. A compound as claimed in claim 1, having the formula:

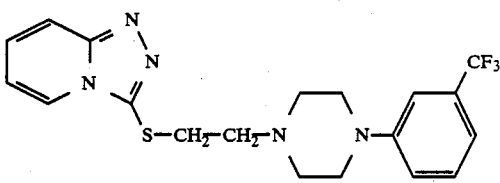

6. A compound as claimed in claim 2, having the formula:

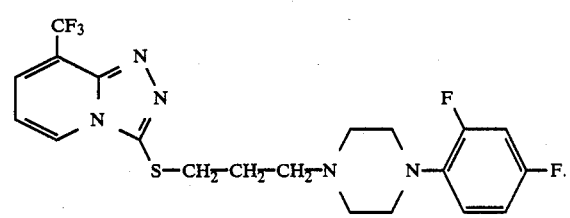

7. A compound as claimed in claim 3, having the formula:

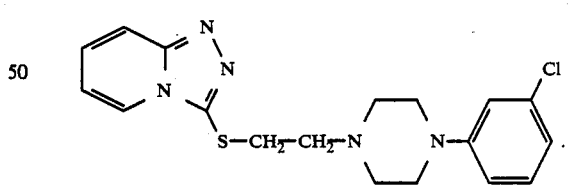

8. A compound as claimed in claim 4, having the formula:

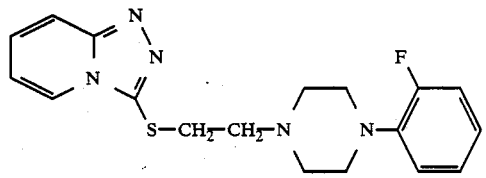

9. A compound having the formula:

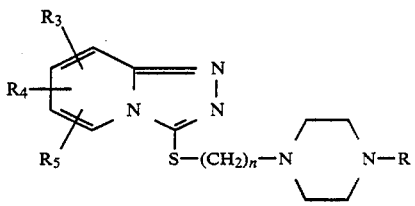

wherein n is an integer from 1 to 8,
R is:
- a phenyl, a phenyl substituted by a lower alkyl having from 1 to 5 carbon atoms, a trifluoromethyl, one or two halogen atoms, a alkoxy, a hydroxyl,
- a diphenyl methane group,
- a pyridine group, a pyridine substituted by a trifluoromethyl, a cyano, a nitro, an amino group;
- a pyrimidine, a pyrimidine substituted by a trihalogenomethyl, a lower alkyl having from 1 to 5 carbon atoms;

each of $R_3$, $R_4$ and $R_5$ is hydrogen, lower alkyl, hydroxyalkyl, hydroxybenzyl group, halogen, trifluoromethyl, methoxy, thiomethyl, nitro, or two of them together form a phenyl ring;
and the non-toxic acid addition salts.

10. A compound having the formula:

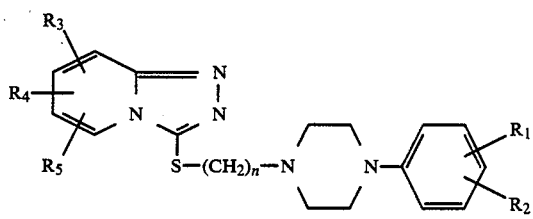

wherein:
- n is an integer from 1 to 8 inclusive;
- each of $R_1$ and $R_2$ is hydrogen, a lower alkyl having 1 to 5 carbon atoms, a trifluoromethyl, a halogen, an alkoxy, a hydroxy;
- each of $R_3$, $R_4$ and $R_5$ is hydrogen, lower alkyl, a hydroxyalkyl, hydroxybenzyl group, a halogen, a trifluoromethyl, a methoxy, a thiomethyl, a nitro, or two of them together form a phenyl ring; and the non-toxic acid addition salts.

11. A compound having the formula:

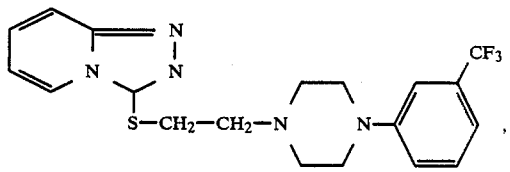

12. A drug having analgesic properties and acting especially on the central nervous system as a minor tranquilizer comprising a therapeutically efficient amount of a compound of the formula:

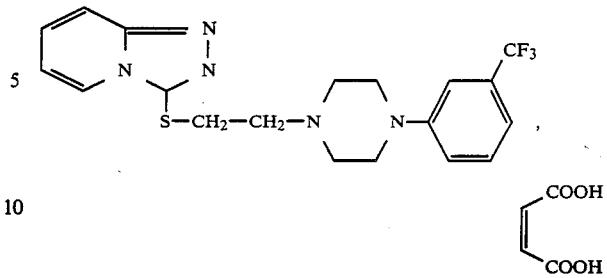

in a pharmaceutically acceptable vehicle or excipient.

13. A drug having analgesic properties and acting especially on the central nervous system as a minor tranquilizer, comprising a therapeutically efficient amount of a compound of the formula:

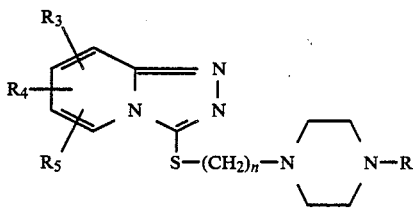

wherein n is an integer from 1 to 8,
R is:
- a phenyl, a phenyl substituted by a lower alkyl having from 1 to 5 carbon atoms, a trifluoromethyl, one or two halogen atoms, a alkoxy, a hydroxyl,
- a diphenyl methane group,
- a pyridine group, a pyridine substituted by a trifluoromethyl, a cyano, a nitro, an amino group;
- a pyrimidine, a pyrimidine substituted by a trihalogenomethyl, a lower alkyl having from 1 to 5 carbon atoms;

each of $R_3$, $R_4$ and $R_5$ is hydrogen, lower alkyl, a hydroxyalkyl, hydroxybenzyl group, a halogen, a trifluoromethyl, a methoxy, a thiomethyl, a nitro, or two of them together form a phenyl ring;
or the non-toxic acid addition salts and a pharmaceutically acceptable vehicle or excipent.

14. A drug having analgesic properties and acting especially on the central nervous system as a minor tranquilizer, comprising a therapeutically efficient amount of a compound of the formula:

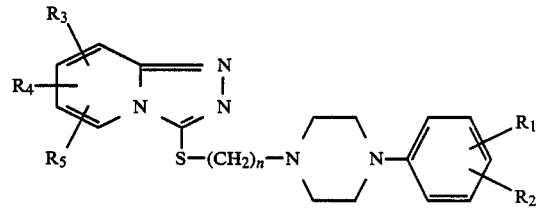

wherein:
- n is an integer from 1 to 8 inclusive;
- each of $R_1$ and $R_2$ is hydrogen, a lower alkyl having 1 to 5 carbon atoms, a trifluoromethyl, a halogen, an alkoxy, a hydroxy;
- each of $R_3$, $R_4$ and $R_5$ is hydrogen, lower alkyl, a hydroxyalkyl, hydroxybenzyl group, a halogen, a trifluoromethyl, a methoxy, a thiomethyl, a nitro, or two of them together form a phenyl ring; or the non-toxic acid addition salts; and a pharmaceutically acceptable vehicle or excipient.

* * * * *